United States Patent [19]

Vives

[11] Patent Number: 4,877,019

[45] Date of Patent: Oct. 31, 1989

[54] INTRAMEDULLARY NAIL AND APPARATUS FOR ITS INSERTION

[76] Inventor: Pierre Vives, Via Clemente Prudenzio, 14/16, 20138 Milan, Italy

[21] Appl. No.: 120,823

[22] Filed: Nov. 16, 1987

[30] Foreign Application Priority Data

Dec. 2, 1986 [IT] Italy .................. 22543 A/86

[51] Int. Cl.⁴ ............................................. A61B 17/58
[52] U.S. Cl. .......................... 128/92 YK; 128/92 YZ; 128/92 YS; 128/92 YY; 128/92 V; 128/92 VD
[58] Field of Search ........... 128/92 Y, 92 YZ, 92 YY, 128/92 YK, 92 YS

[56] References Cited

U.S. PATENT DOCUMENTS

| | | | |
|---|---|---|---|
| 3,717,146 | 2/1973 | Halloran | 128/92 YZ |
| 4,237,875 | 12/1980 | Termanni | 128/92 BA |
| 4,446,857 | 5/1984 | Otte et al. | 128/92 YZ |
| 4,475,545 | 10/1984 | Ender | 128/92 YY |
| 4,541,424 | 9/1985 | Grosse et al. | 128/92 YY X |
| 4,621,628 | 11/1986 | Brudermann | 128/92 VD |
| 4,622,959 | 11/1986 | Marcus | 128/92 YZ |
| 4,705,027 | 11/1987 | Klaue | 128/92 YY |

FOREIGN PATENT DOCUMENTS

| | | | |
|---|---|---|---|
| 824239 | 12/1951 | Fed. Rep. of Germany | 128/92 YZ |
| 913228 | 6/1954 | Fed. Rep. of Germany | 128/92 YZ |
| 1930354 | 10/1978 | Fed. Rep. of Germany | 128/92 YZ |

OTHER PUBLICATIONS

Journal of Bone & Joint Surgery, vol. 33A, 4/1951, p. 21.

*Primary Examiner*—Robert A. Hafer
*Assistant Examiner*—Kevin G. Rooney
*Attorney, Agent, or Firm*—Bucknam and Archer

[57] ABSTRACT

An intramedullary nail comprises a tubular body (1) having a hexagonal cross section and is curved along its length from a proximal end to a distal end, with a frusto-conically tapering portion (3) at the distal end. Adjacent the distal end portion (3) are a plurality of holes (6) and adjacent the proximal end are a plurality of slots (7) for receiving fixing screws or locking pins. A longitudinal slot is provided along one corner of the hexagonally shaped nail to increase the flexural elasticity of the nail in the longitudinal direction. A specific apparatus for use in insertion of the nail into the bone and for locating the holes in its ends is also disclosed.

1 Claim, 7 Drawing Sheets

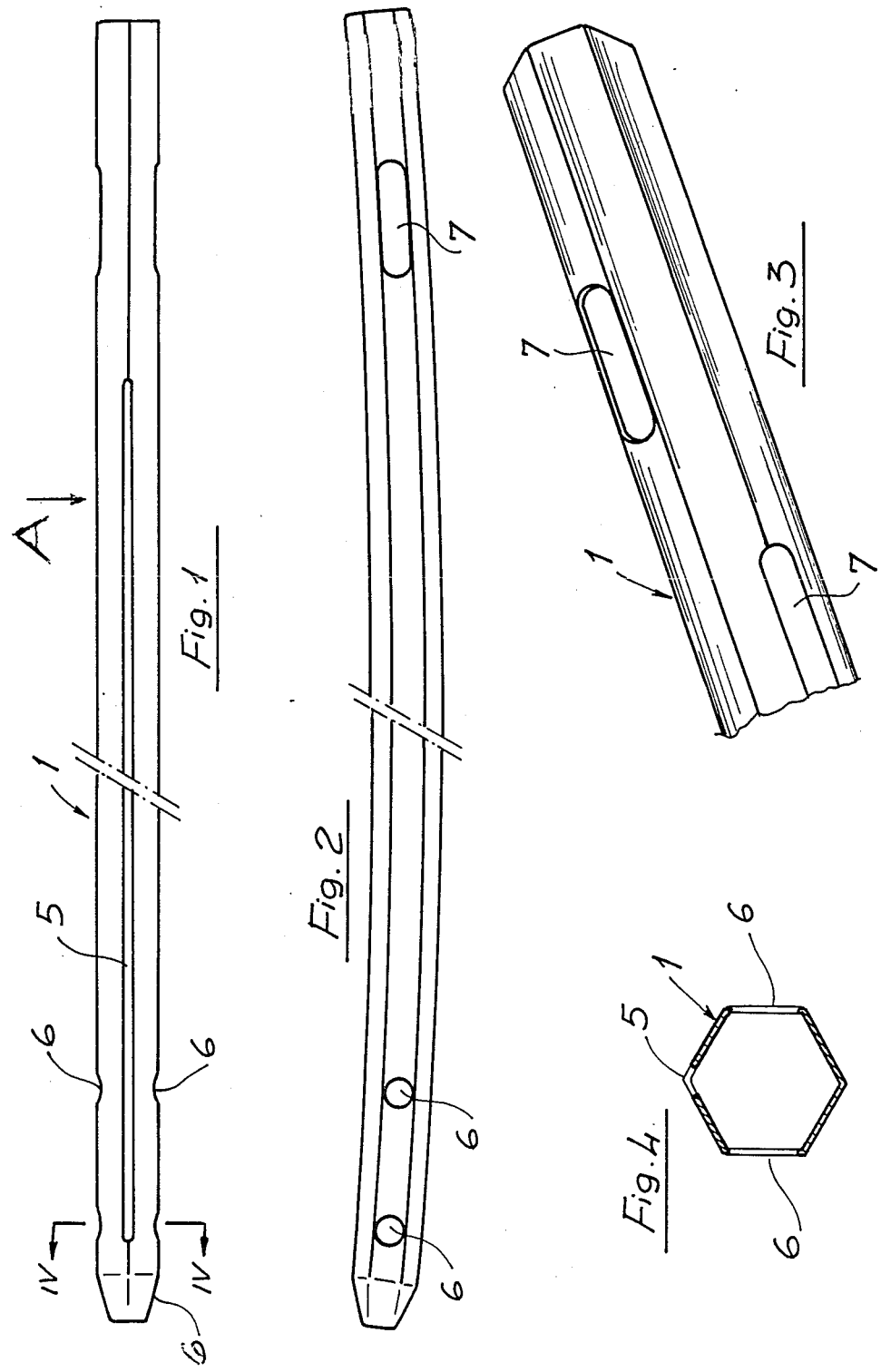

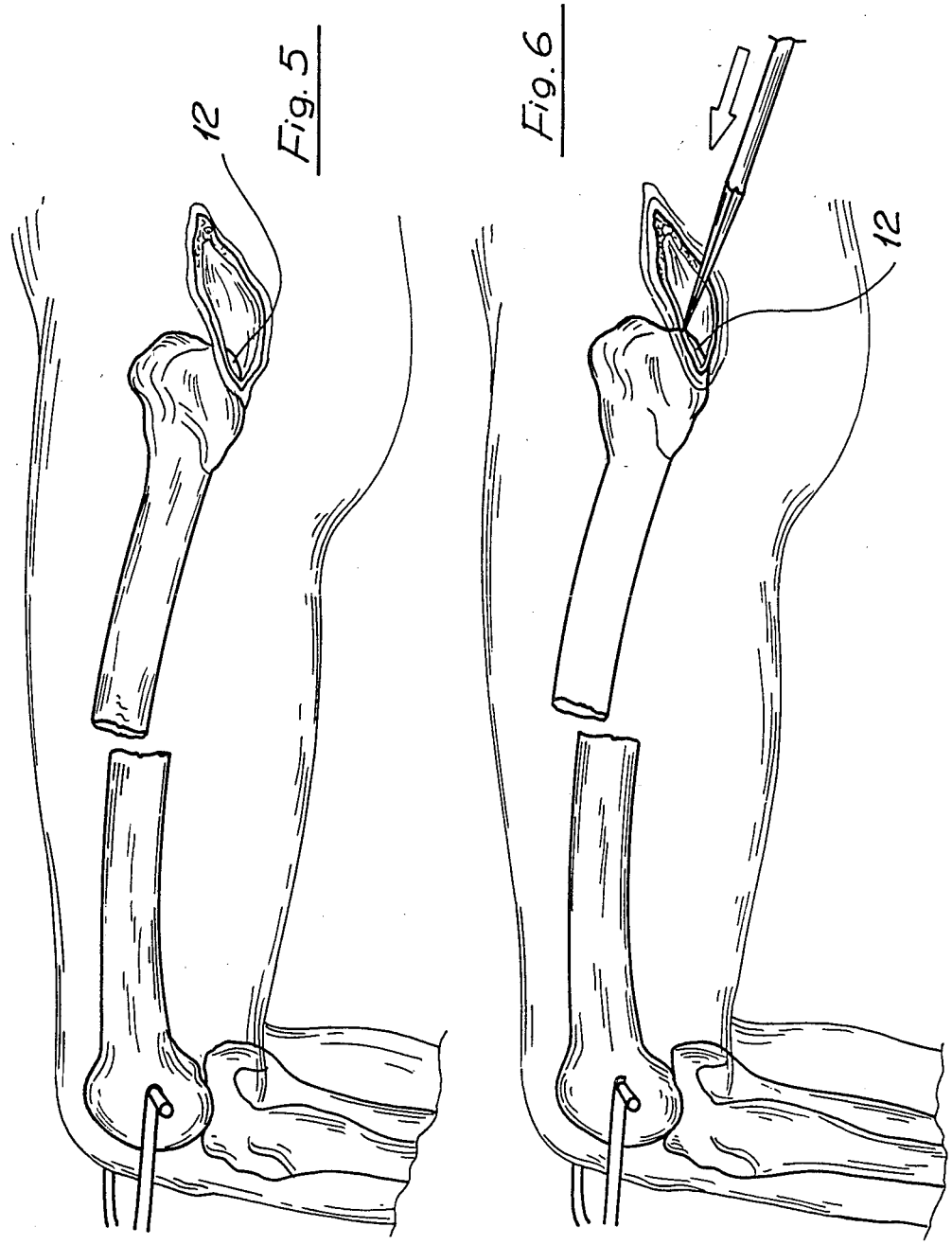

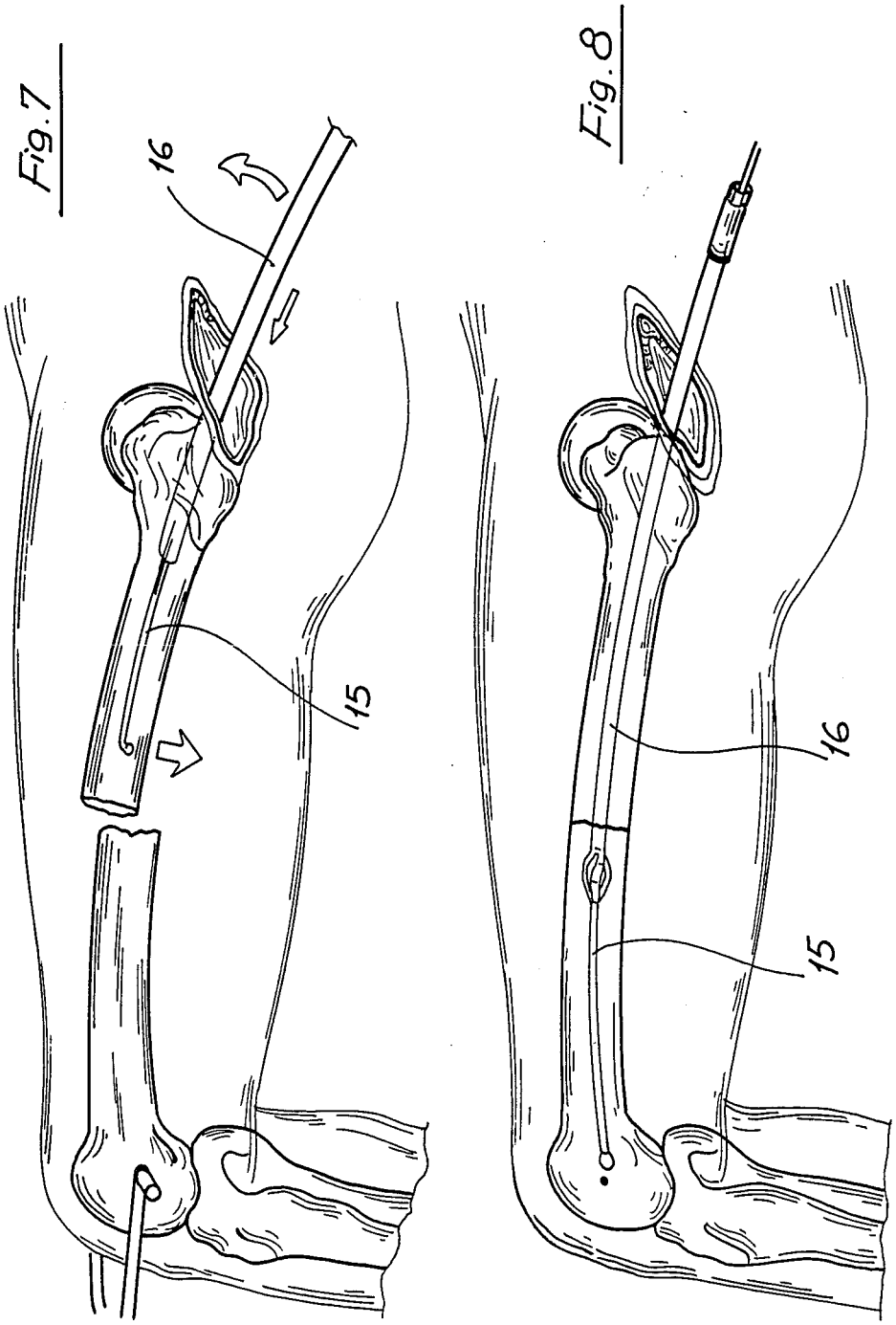

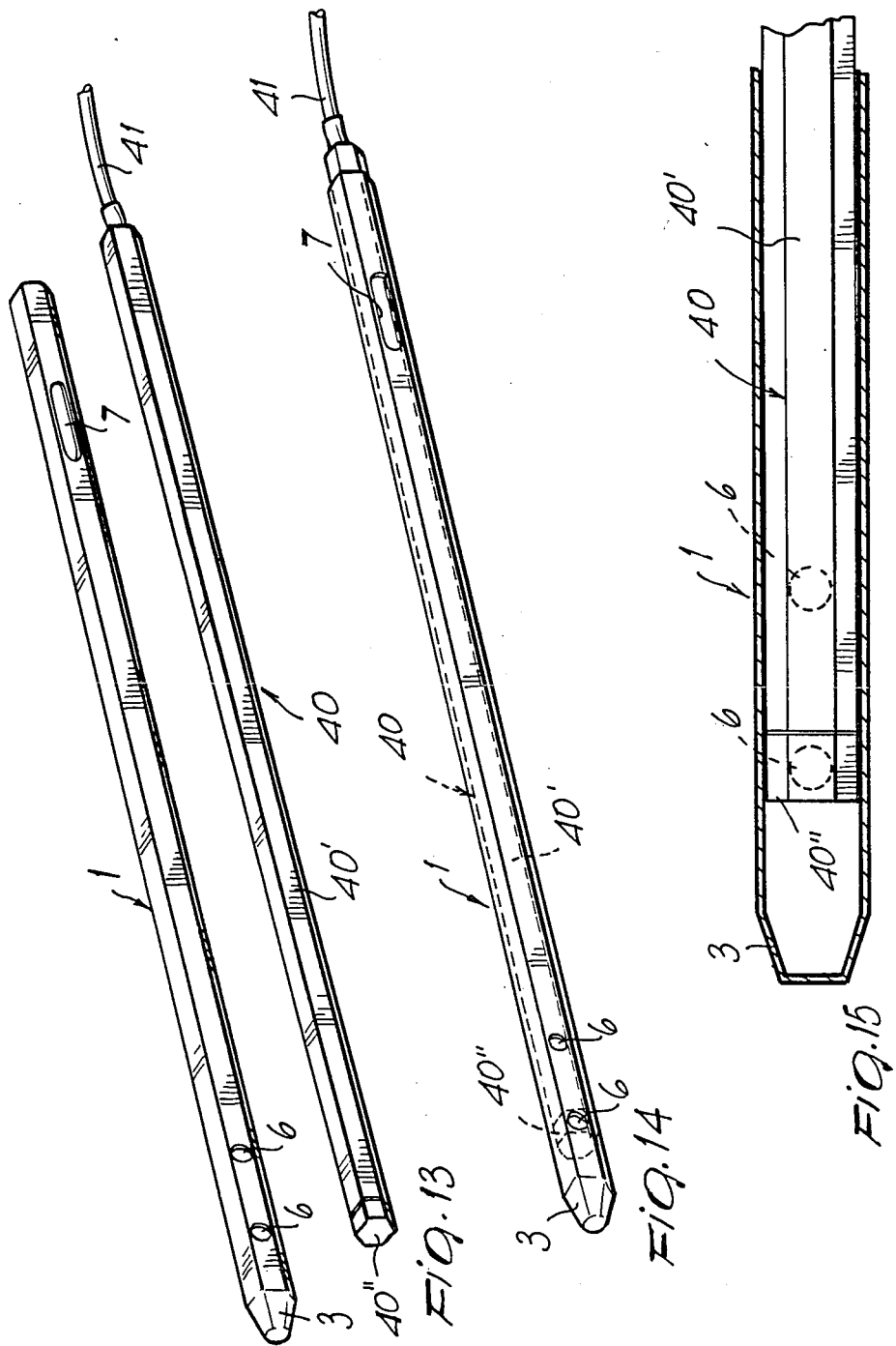

INTRAMEDULLARY NAIL AND APPARATUS FOR ITS INSERTION

The present invention relates to an intramedullary nail, and to apparatus for its insertion into a bone.

One of the techniques known for the treatment of bone fractures and, in particular for fracture of the femur provides for the insertion of a nail into the bone, and in particular, into the medullary canal.

Various types of nails for this purpose are known, these being of circular or tri-flangiate cross section (the latter being known as a Kuntscher nail) which although universally adopted have the disadvantage of requiring relatively high material thicknesses to be able to guarantee the necessary mechanical strength both under torsion aand compression. The use of nails having a large material thickness involves certain disadvantages the most important of which is the limited flexural elasticity which such a nail has.

Moreover, with nails of known type there is often encountered difficulty in fitting the fixing screws which are used at each end to secure it to the bone once introduced therein, in that it is not always possible to obtain accurate centering of the fixing screws in the bone with respect to holes for receiving them which must be provided in the nail itself before it is introduced.

The object of the invention is to overcome the above-mentioned disadvantage by providing an intramedullary nail which has a very high mechanical strength with only a relatively slender wall thickness so that twisting forces can be resisted and any twisting which does occur during insertion can be compensated so that holes for fixing the screws or pins to be introduced, after insertion of the nail, from outside the bone, can be centered always with extreme precision with respect to the holes in the nail itself.

According to the present invention, therefore, there is provided an intramedullary nail, characterised in that it comprises a tubular body of hexagonal cross section having a distal end and a proximal end, being curved along its length, and having a frustoconical taper at the distal end.

A particular advantage of the invention is that of providing a nail which is easily insertable, for example, into the interior of the femoral medullary canal, and which strongly resists, even in some cases absolutely resists, unwanted rotation about its one axis during insertion into the bone thereby contributing to an improvement in the precision with which the holes for receiving the screws or pins can be located.

Another advantage of the present invention is that of providing an intramedullary nail which, by its particular constructional characteristics, is able to offer the widest guarantees of reliability and safety in use.

The present invention also has the advantage that embodiments thereof can be formed easily, starting from elements and materials which are commonly commercially available and, therefore, of relatively low cost.

One embodiment of the present invention will now be more particularly described, by way of example, with reference to the acompanying drawings, in which:

FIG. 1 is a side view of an intramedullary nail formed as an embodiment of the invention;

FIG. 2 is a side view of the nail of FIG. 1 viewed from the direction of the arrow A of FIG. 1;

FIG. 3 is a perspective view of the proximal end of the nail of FIG. 1;

FIG. 4 is a section taken on the line IV—IV of FIG. 1;

FIG. 5 is a schematic diagram illustrating the cutaneous incision which is made prior to re-positioning and resetting a fractured femur using an intramedullary nail;

FIG. 6 is a schematic diagram illustrating the bone incision which is made at the top of the greater trochanter;

FIG. 7 is a schematic diagram illustrating the introduction of a guide wire into the medulla;

FIG. 8 is a schematic diagram illustrating the internal boring of the bone tissue;

FIG. 13 is a perspective view illustrating the nail and a position indicator probe cooperating therewith;

FIG. 14 represents the nail with the probe introduced therein;

FIG. 15 is a partially broken away cross-sectional view illustrating the probe arranged in its nail distal-end hole sensing position;

Figure 9:
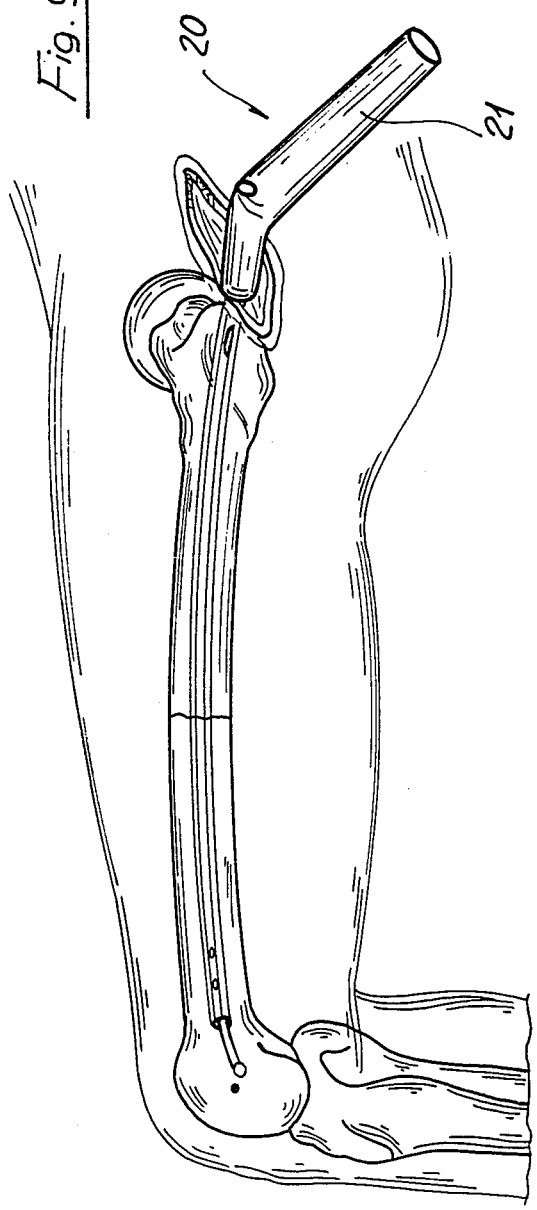
FIG. 9 is a schematic diagram illustrating the introduction of the nail of the invention into the bore.

Referring first to FIGS. 1 to 4 of the drawings, the intramedullary nail of the invention comprises an elongate hollow tubular body, generally indicated with the reference numeral 1, curved along its length with a curvature having a relatively large radius. The tubular body 1 has, in cross section, a substantially hexagonal shape with a wall thickness which can be selected at will upon manufacture to adapt it to the requirements of strength and elasticity required in use. For example, this wall thickness may vary between 0.5 and 2 mm.

For the production of the nail of the invention traditional materials used in surgery can be used, for example, metals such as titanium and its alloys, polymeric materials, composite materials, ceramic materials, or a combination of any of the above-mentioned materials.

The tubular body 1 has a distal end 3 which has a substantially frustoconical tapering shape to facilitate the introduction of the nail into the bone.

The flexural elasticity of the tubular body 1 is modified by the provision of a longitudinal slot 5 the length and width of which can be selected in dependence on the modifying influence it is intended to achieve. At its distal end the tubular body also has one or more holes 6, whilst at its proximal end there are formed one or more slots 7 intended to receive the screws or through pins intended to fix the nail in position in the bone.

Utilisation of a hexagonal cross section is of considerable importance in that it presents a strong increase both in the capacity to resist torsion and the mechanical resistance to torsion over those of nails of known type, for example, those having a tri-flangeate section.

To insert the nail 1 into the medullary canal the usual preparation is made by means of cutaneous incision at the head of the femur as illustrated in FIG. 5; then, by means of a drill 10, an incision is effected at the end of the greater trochanter 12 as illustrated in FIG. 6. Following this, as illustrated in FIG. 7, the guide wire 15 is introduced, which is pushed into the medulla until it reaches the region of the break in the bone, and then, once the fracture is re-positioned, the complete introduction of the wire guide is effected. The final stage is the preparation, as illustrated in FIG. 8, is by means of an appropriate sheath 16, to effect boring of the hole to bring it to the desired dimension compatible with the dimension of the nail to be introduced.

Insertion takes place from the apex of the greater trochanter by striking from the outside with the aid of a beater 20 as illustrated in FIG. 9. The beater has a handle body 21 which, at the end facing towards the zone of introduction into the bone, is provided with a threaded portion 20' in which is insertable an adapter 20" onto which the nail can be threaded; obviously, such adapter will have an hexagonal section corresponding to the external section of the intramedullary nail. The internal hole has the object of causing the nail on the beater to slide along a guide wire, which facilitates the insertion into the medullary canal.

Figure 10:
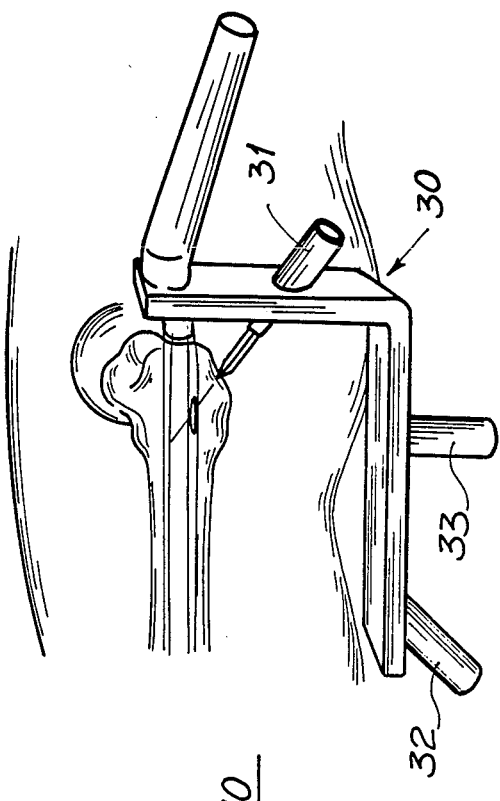
FIG. 10 is a schematic diagram illustrating the incision of the external bone cortex using a guide bracket.
Figure 11:
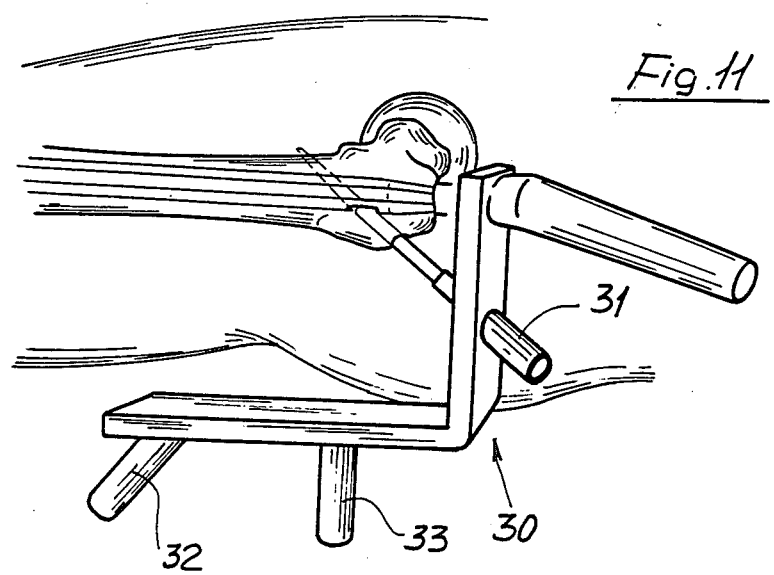
FIG. 11 is a schematic diagram illustrating the boring of the external and internal bone cortex for the application of the fixing screw.
Figure 12:
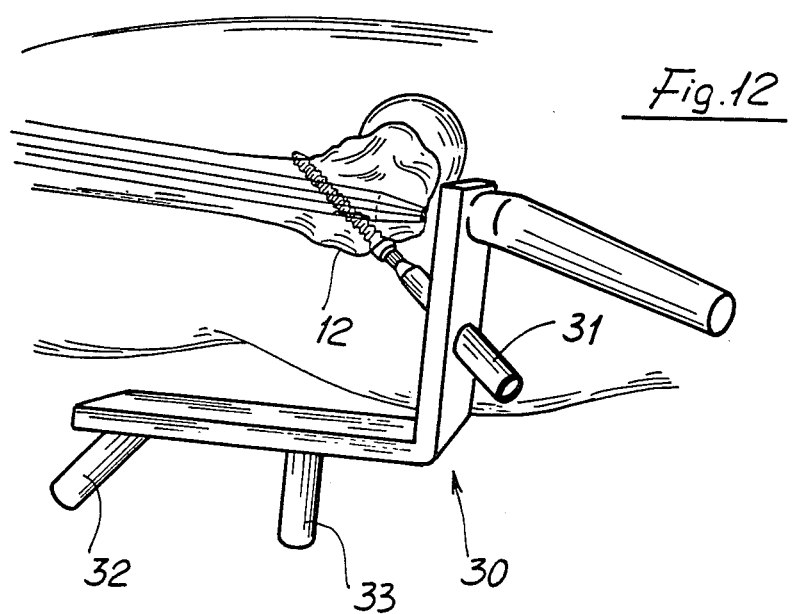
FIG. 12 is a schematic diagram illustrating the application of the fixing screw at the proximal end, effected with the aid of the guide bracket.
Figure 16:
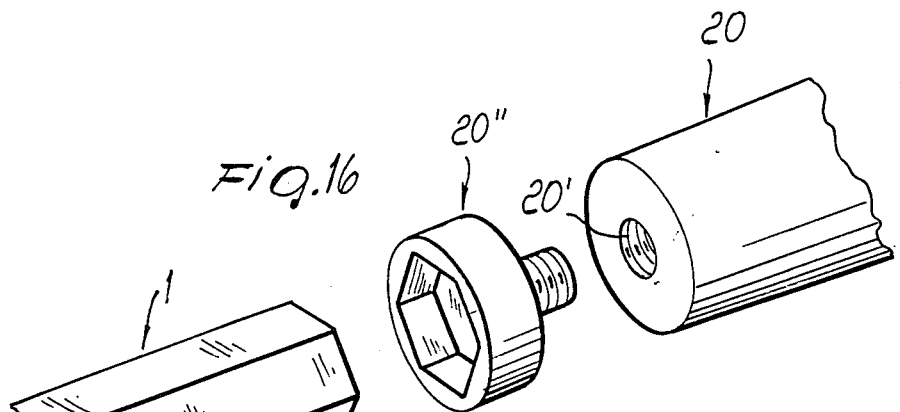
FIG. 16 is a broken away partial view illustrating, in their disassembled condition, a beater member-adapter assembly for force introducing the nail into an intramedullary channel.
Figure 17:
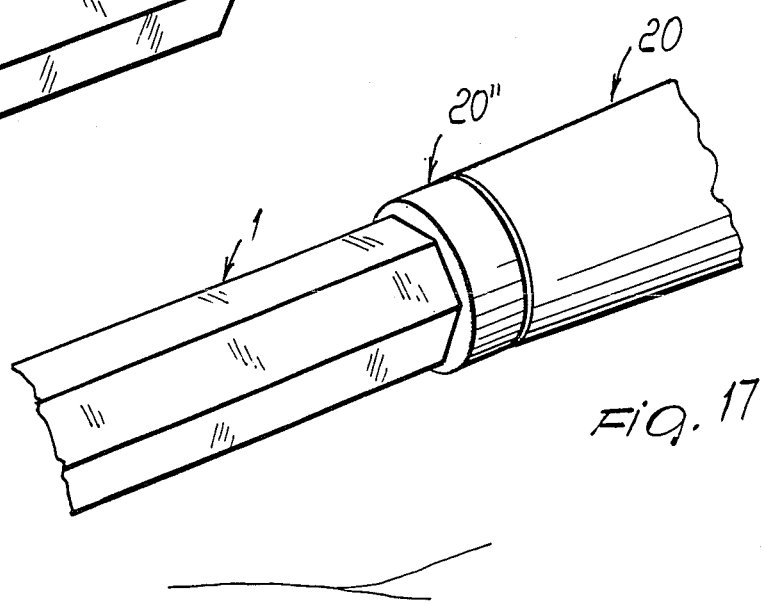
FIG. 17 represents the assembly of FIG. 16 with the beater member and adapter in their engaged condition.
Figure 18:
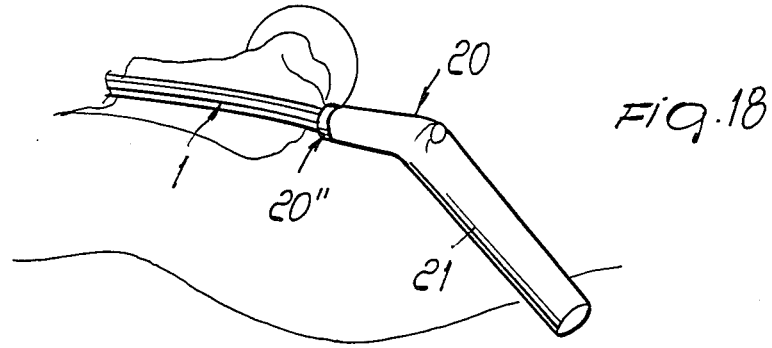
FIG. 18 is a detail perspective view illustrating the beater member during the nail introducing step.

In order to fix the nail to the bone cortex, by means of screws, if required, there is provided a guide bracket 30 illustrated in FIG. 10, which facilitates the insertion of the screws in the exact position with respect to the nail, obviously once the nail has been inserted into the medullary canal. To effect insertion of the oblique proximal screw the guide bracket 30 has inclined guide bushes 31 and 32 having different inclinations with respect to the longitudinal axis of the nail in such a way as to be able to provide an optimum insertion path.

The guide bracket is generally L-shape and the said inclined guide bushes 31 and 32 are positioned one on each arm; on the arm other than that connected to the end of the nail is fitted a cylindrical guide 33 which allows, if required, the insertion of a pin in a direction substantially perpendicular to the length of the bone.

To obtain centring and positioning of the distal screws in the holes 6 in the distal end of the nail 1 there is utilised electromechanical instrumentation (not shown) which provides for the introduction, from the proximal end, of a position indicator probe 40 constituted by an external guide casing 40' of metal or plastics, which has an hexagonal cross section of a size which fits the internal shape of the tubular body 1. The guide casing contains electronic microcircuits (schematically indicated by the probe end block 40" and which can be based, for example, on well known Hall effect chips) which, when activated, are able to generate a small electrical current and consequently a magnetic field.

The probe is introduced into the nail, after it has been positioned in the bone, and fed along towards the distal end until it is located on the axis of one of the distal holes of the nail. Any twist which the nail may have aquired during insertion are compensated by corresponding rotation of the probe guided by its hexagonal external form which matches that of the internal shape of the nail itself.

Two reference notches (not shown), one on the nail and one on a connecting "umbilical cord" 41 leading out from the probe, ensure that this latter is in position on the distal hole. Once congruence between the axis of the hole and the probe has been established it is only necessary to identify this axis and for this purpose external permanent magnets of circular form pierced at the centre (toroidal magnets), are used. When the axis of the magnet is positioned in coincidence with the axis of the probe it is possible to receive a luminous signal on the screen of an oscilloscope exactly at the centre thereof, the signal being visible at other positions of the screen when the relative position between the magnet and the probe differs from exact alignment. The exact centring of the signal on the screen ensures the perfect axial coincidence of the axis of the hole and the axis of the magnet so that it is now possible, once the magnet is fixed in the position found, to use the central hole thereof or a suitable external support connected to it, as a guide in making the hole in the bone through which the screw will be fitted.

Obviously, it is also possible to utilise a solid cylindrical magnet in place of the hollow one, as indicated above, in that the direction of the axis of the magnetic field used for locating the distal holes remains unaltered. The operation is completed by piercing the bone and inserting the screw through this latter and the intramedullary nail.

The intramedullary nail of the invention, having a hexagonal cross section, allows a greater mechanical strength to be obtained together with an improved positioning and fixing of the nail itself thanks to the greater facility in finding the holes for the application of the fixing screws.

I claim:

1. An intramedullary nail, comprising an elongated tubular body of hexagonal cross section having a distal end and a proximal end, with a frustoconical taper at said distal end, said elongated tubular body further having a side wall including at least a hole therein adjacent said distal end and at least a slot adjacent said proximal end, wherein said elongated tubular body has a slot extending in a longitudinal direction of said tubular body and formed for a given length along a longitudinal corner defined by two adjoining sides of said hexagonal cross-section, said longitudinal slot being so designed and arranged as to increase flexural elasticity of said elongated tubular body in said longitudinal direction.

* * * * *